United States Patent
Govari et al.

(10) Patent No.: US 11,793,565 B2
(45) Date of Patent: Oct. 24, 2023

(54) DETECTING ELECTRODE CONTACT USING ABSOLUTE AND RELATIVE THRESHOLDS

(71) Applicant: BIOSENSE WEBSTER (ISRAEL) LTD., Yokneam (IL)

(72) Inventors: Assaf Govari, Haifa (IL); Andres Claudio Altmann, Haifa (IL); Lilah Marziano, Ganey-Tikva (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 387 days.

(21) Appl. No.: 17/035,845

(22) Filed: Sep. 29, 2020

(65) Prior Publication Data
US 2022/0096148 A1    Mar. 31, 2022

(51) Int. Cl.
*A61B 18/12* (2006.01)
*A61B 18/14* (2006.01)
*A61B 18/00* (2006.01)

(52) U.S. Cl.
CPC ...... *A61B 18/1492* (2013.01); *A61B 18/1206* (2013.01); *A61B 2018/0072* (2013.01); *A61B 2018/00351* (2013.01); *A61B 2018/00363* (2013.01); *A61B 2018/00577* (2013.01); *A61B 2018/00613* (2013.01); *A61B 2018/00666* (2013.01); *A61B 2018/00672* (2013.01); *A61B 2018/00678* (2013.01); *A61B 2018/00827* (2013.01); *A61B 2018/00875* (2013.01);
(Continued)

(58) Field of Classification Search
CPC ............ A61B 18/1492; A61B 18/1206; A61B 2018/00351; A61B 2018/00363; A61B 2018/00577; A61B 2018/00613; A61B 2018/00666; A61B 2018/00672; A61B 2018/00678; A61B 2018/0072; A61B 2018/00827; A61B 2018/00875; A61B 2018/00898; A61B 2018/126; A61B 2018/1407; A61B 2018/1467
See application file for complete search history.

(56) References Cited

U.S. PATENT DOCUMENTS 5,514,139 A    5/1996  Goldstein
8,147,485 B2 *  4/2012  Wham ............... A61B 18/1206
                                                606/51
(Continued)

FOREIGN PATENT DOCUMENTS

WO    WO2014145903 A2    9/2014

OTHER PUBLICATIONS

European Search Report for corresponding EPA No. 21199367.0 dated Jan. 3, 2022.

*Primary Examiner* — Daniel W Fowler

(57) ABSTRACT

A medical apparatus includes a probe configured for insertion into a body of a patient and including three or more electrodes arrayed along a distal portion of the probe and configured to contact tissue within the body. An electrical signal generator is configured to apply between a selected pair of the electrodes signals having an amplitude sufficient to ablate the tissue contacted by the pair of the electrodes. A controller is configured to measure an electrical current flowing through at least one of the electrodes not included in the selected pair while applying the signals, and to issue a notification indicating that the tissue was inadequately ablated if the measured electrical current exceeds a preset threshold.

16 Claims, 2 Drawing Sheets

(52) U.S. Cl.
CPC .............. *A61B 2018/00898* (2013.01); *A61B 2018/126* (2013.01); *A61B 2018/1407* (2013.01); *A61B 2018/1467* (2013.01)

(56) References Cited

U.S. PATENT DOCUMENTS

| | | | |
|---|---|---|---|
| 9,297,845 B2 | 3/2016 | Mathur | |
| 9,561,377 B2 | 2/2017 | Gunderson | |
| 9,999,465 B2* | 6/2018 | Long | A61B 18/1206 |
| 2006/0161149 A1* | 7/2006 | Privitera | A61B 5/0538 |
| | | | 606/41 |
| 2011/0245888 A1 | 10/2011 | Badelt | |
| 2012/0029529 A1* | 2/2012 | Jun | A61B 34/30 |
| | | | 606/130 |
| 2013/0289551 A1* | 10/2013 | Condie | A61B 18/1233 |
| | | | 606/33 |
| 2014/0266235 A1* | 9/2014 | Mathur | A61N 1/36139 |
| | | | 324/509 |
| 2014/0276769 A1 | 9/2014 | Goertzen | |
| 2016/0199116 A1* | 7/2016 | Jameson | A61B 18/00 |
| | | | 606/41 |
| 2017/0035499 A1* | 2/2017 | Stewart | A61N 1/327 |
| 2018/0235686 A1 | 8/2018 | Sahakian | |
| 2019/0307500 A1 | 10/2019 | Byrd | |

* cited by examiner

DETECTING ELECTRODE CONTACT USING ABSOLUTE AND RELATIVE THRESHOLDS

FIELD OF THE INVENTION

The present invention relates generally to medical equipment, and particularly to apparatus and methods for electrical ablation of tissue.

BACKGROUND

Irreversible electroporation (IRE) and radio frequency ablation (RFA) are soft tissue ablation techniques, which are commonly performed by inserting a catheter or thin probe into the tissue, and applying high-frequency electrical currents from the tip of the catheter or probe to the tissue.

In IRE, short pulses of strong electrical fields are applied to create permanent and hence lethal nanopores in the cell membrane, thus disrupting the cellular homeostasis (internal physical and chemical conditions). Typical pulse widths are from 0.5 to 5 µs, the pulse frequencies are from 50 kHz to 1 MHz, and pulse amplitudes are from 200 to 2000 V. Cell death following IRE results from apoptosis (programmed cell death) and not necrosis (cell injury, which results in the destruction of a cell through the action of its own enzymes) as in other thermal and radiation-based ablation techniques. IRE is commonly used in tumor ablation in regions where precision and conservation of the extracellular matrix, blood flow and nerves are of importance.

In RFA, a high-power alternating current is applied to tissue so that the heat generated by the current ablates the tissue. RFA is applied, for example, in ablating electrical conduction pathways of the heart, tumors, and other dysfunctional tissues. RFA typically uses currents with amplitude in the range of 0 to 200 V and frequency in the range of 350-500 kHz.

SUMMARY

Embodiments of the present invention that are described hereinbelow provide improved systems and methods for electrical ablation of tissue.

There is provided, in accordance with an embodiment of the present invention, a medical apparatus, including a probe configured for insertion into a body of a patient and including three or more electrodes arrayed along a distal portion of the probe and configured to contact tissue within the body. An electrical signal generator is configured to apply, between a selected pair of the electrodes, signals having an amplitude sufficient to ablate the tissue contacted by the pair of the electrodes. A controller is configured to measure an electrical current flowing through at least one of the electrodes not included in the selected pair while applying the signals, and to issue a notification indicating that the tissue was inadequately ablated if the measured electrical current exceeds a preset threshold.

In some embodiments, the controller is configured to issue a first notification indicating that the tissue was inadequately ablated if the measured electrical current exceeds a first threshold, and to issue a second notification indicative of a parasitic current flow between the at least one of the electrodes and one of the selected pair of the electrodes when the measured electrical current does not exceed the first threshold but does exceed a second threshold, which is lower than the first threshold. In a disclosed embodiment, the second threshold is less than half the first threshold. Additionally or alternatively, the second threshold is adjustable by a user.

Typically, the controller is configured to measure and monitor respective currents flowing through multiple electrodes that are not in the selected pair.

In a disclosed embodiment, the amplitude of the signals is sufficient to cause irreversible electroporation (IRE) of the tissue contacted by the selected pair of the electrodes.

Additionally or alternatively, the distal portion is flexible, and is configured for insertion into a heart of the patient. In one embodiment, the distal portion is configured to form a loop within the heart.

There is also provided, in accordance with an embodiment of the present invention, a method for medical treatment, which includes inserting a probe into a body of a patient, wherein the probe includes three or more electrodes arrayed along a distal portion of the probe. At least a selected pair of the electrodes of the probe is brought into contact with tissue within the body. Signals are applied between the selected pair of the electrodes with an amplitude sufficient to ablate the tissue contacted by the selected pair. An electrical current flowing through at least one of the electrodes not included in the selected pair is measured while applying the signals. A notification indicating that the tissue was inadequately ablated is issued if the measured electrical current exceeds a preset threshold.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Figure 1:
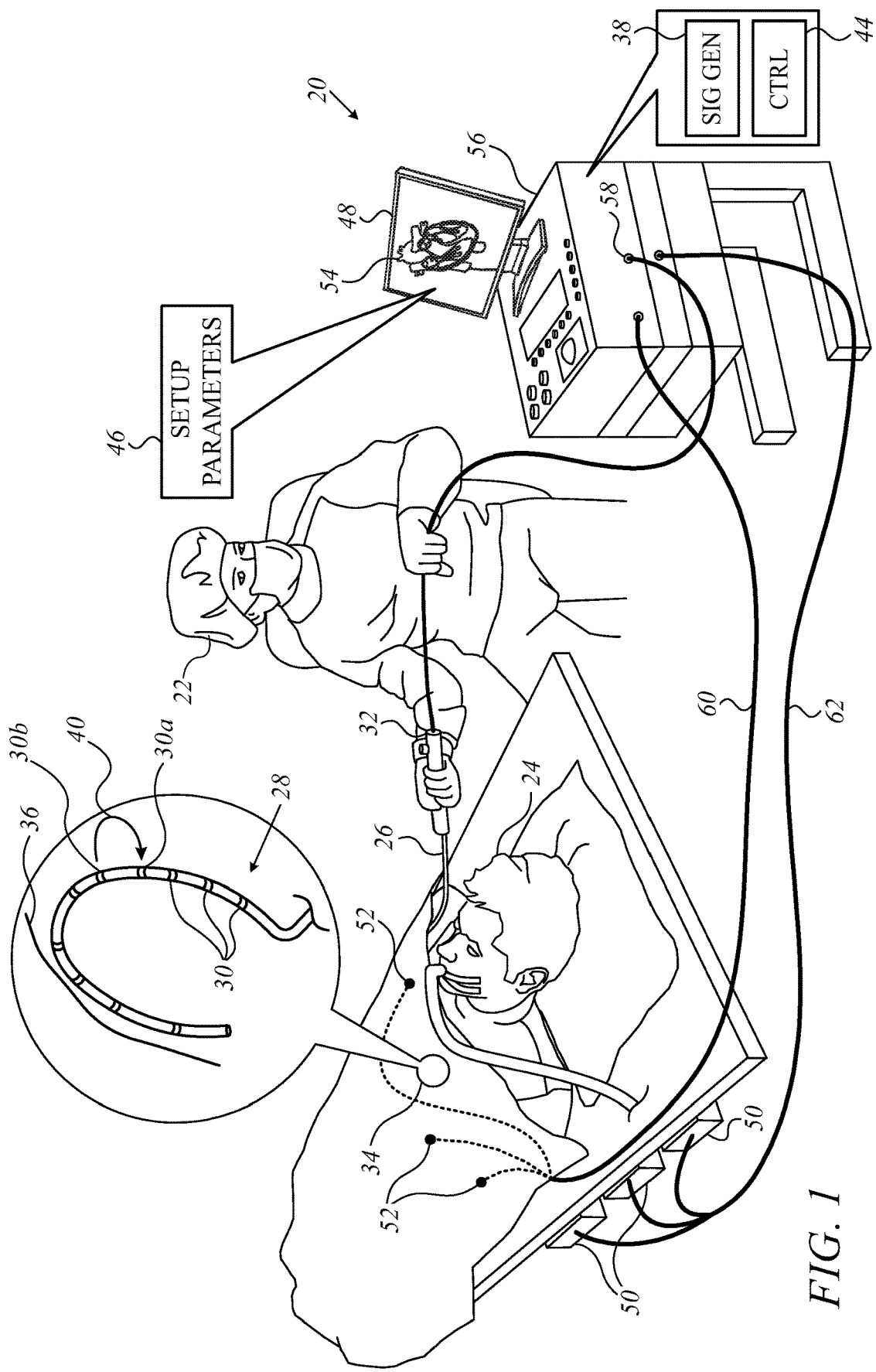
FIG. 1 is a schematic pictorial illustration of a medical apparatus in the course of a medical ablation procedure, in accordance with an exemplary embodiment of the invention.

In medical electrical ablation, an electrical current is driven through the tissue of a subject. In IRE, the current generates nanopores in cell membranes, whereas in RFA the current heats the tissue. The current is injected into the tissue, for example, through electrodes that are mounted on a catheter, which is inserted into the subject's body. The electrodes are connected to a current source; when the electrodes contact desired parts of the tissue, the current source is activated, and ablation takes place. Both IRE and bipolar RFA utilize pairs of electrodes, so that the ablation current flows into the tissue through one electrode, and returns through the other electrode. In unipolar RFA, the ablation current flows from one electrode in the catheter into the tissue, as in bipolar RFA, but returns through the body of the subject via a common electrode attached to the skin of the subject.

When using a flexible catheter with multiple electrodes, for example a catheter with a distal portion configured to form a loop, such as a Lasso® or nMARQ®-catheter (produced by Biosense Webster Inc., Irvine, Calif.), some electrodes may inadvertently come too close to others, and possibly even come into mutual contact. Specifically, if a given pair of electrodes is used for the ablation, and a third electrode comes too close to either of the electrodes of the pair, a substantial portion of the ablation current may be shunted to the third electrode, thus reducing or possibly even annulling the intended effect of the ablation. The physician administering the ablation may not be aware of this effect on the ablation, and thus will not realize that correction is required. This problem is particularly significant in IRE, in which inadequate current may result in electroporation that is not irreversible; but it is also encountered in other types of therapy, such as RFA.

The embodiments of the present invention that are described herein address this problem by monitoring the currents flowing through those catheter electrodes that are not participating in the ablation at any given time during the procedures. These embodiments provide a medical apparatus comprising a probe, an electrical signal generator, and a controller. The probe, such as a catheter, comprises three or more electrodes arrayed along the distal portion of the probe and configured to contact tissue within the body. The electrical signal generator applies electrical signals between selected pairs of the electrodes, with amplitude sufficient to ablate the tissue contacted by the pair of the electrodes.

To ensure that the resulting electrical current is actually flowing through the tissue and not shunted to other electrodes, the controller measures the current flowing through these other electrodes while applying the signals. The current flow can be measured directly, or the current can be measured indirectly, for example by measuring the voltages on the electrodes as an indicator of the current flowing through them; and references to "measuring an electrical current" in the present description and in the claims should be understood to encompass any and all modes of measurement that are known in the art, whether direct or indirect. If the measured current exceeds a preset threshold, the controller issues a notification indicating that the tissue may have been inadequately ablated. The notification prompts the operator of the apparatus to check and correct the disposition of the distal portion of the probe in the body, after which the ablation can be completed as needed.

In the disclosed embodiments, one or more current thresholds may be set. A single threshold is useful in itself in alerting the physician to the possibility of inadequate ablation, but the use of two thresholds provides a finer level of guidance. For example, a first threshold may be set at a high level, such that a current flowing through a given electrode in excess of this threshold indicates that the electrode is probably in physical contact with one of the pair of ablation electrodes. A second threshold may be set at a lower level to indicate that the given electrode is sufficiently close to one of the pair of ablation electrodes so as to draw a parasitic current flow through the third electrode, which can have a significant effect on the desired ablation current, even if the third electrode is not in physical contact with the ablation electrodes. For example, the second threshold may be set at a value that is half of the first threshold, or possibly less.

Based on the notifications issued by the controller, the physician administering the ablation may decide on further actions. If the current to a given electrode exceeds the first threshold, the physician is notified, and may assume that the ablation has been inadequate. In this case, the physician will typically take an action such as adjusting the catheter, and repeating the ablation. If the current for a given electrode is less than the first threshold but exceeds the second threshold, the physician is notified. The notification enables the physician to accept or reject the ablation, and also to adjust, or leave as is, the second threshold.

FIG. 1 is a schematic pictorial illustration of a medical apparatus 20 in the course of a medical ablation procedure, in accordance with an exemplary embodiment of the invention. A physician 22 performs the procedure on a subject 24, using an ablation catheter 26 whose distal portion 28 comprises multiple ablation electrodes 30. The ablation procedure may comprise either an IRE procedure or a bipolar RFA procedure, or possibly a combination of both kinds of ablation procedures.

In the pictured embodiment, physician 22 is performing a cardiac ablation procedure using medical apparatus 20. To begin the procedure, physician 22 inserts catheter 26 into the body of subject 24, and then navigates the catheter, using a control handle 32, to an appropriate site within, or external to, a heart 34 of subject 24. Subsequently, the physician brings distal portion 28 into contact with tissue 36, such as myocardial or epicardial tissue, of heart 34. Physician 22 selects a pair of electrodes 30a and 30b for the ablation. Physician 22 then actuates an electrical signal generator (SIG GEN) 38 to generate ablation signals 40, with signal parameters selected, for example, to serve as either IRE signals or RFA signals, or a combination of both. Signals 40 are carried through catheter 26, over different respective channels, to ablation electrodes 30a and 30b, such that the ablation current flows from one of the electrodes in the pair through tissue 36 of subject 24, and returns through the other electrode of the pair.

Medical apparatus 20 further comprises a controller (CTRL) 44. Controller 44 receives from physician 22 (or another user), prior to and/or during the ablation procedure, setup parameters 46 for the procedure. For example, using one or more suitable input devices, such as a keyboard, mouse, or touch screen, physician 22 defines the ablation mode (IRE, RFA), the parameters of the ablation signals (for example power, duration), and the electrode pair to be used for the ablation. Physician 22 may also define the first and second thresholds for detecting a parasitic leakage of ablation current to any electrode that is not included in the selected pair of electrodes.

Physician 22 may also input, using the above mentioned input devices, additional setup parameters 46 for ablation signal 40, such as a maximum power, a maximum current amplitude, a maximum voltage amplitude, a duration of the signal, and/or any other relevant parameters. In response to receiving setup parameters 46, controller 44 communicates with signal generator 38, so that the signal generator generates signals 40 in accordance with the setup parameters. Additionally, the controller 44 may display the setup parameters on a display 48 (which may comprise the aforementioned touch screen).

Controller 44 tracks the respective positions of ablation electrodes 30 in the subject's body during the procedure, using any suitable tracking technique. For example, distal portion 28 may comprise one or more electromagnetic position sensors (not shown), which, in the presence of an external magnetic field generated by one or more magnetic-field generators 50, output signals that vary with the positions of the sensors. Based on these signals, the controller 44 may ascertain the positions of the electrodes. Alternatively, for each electrode, controller 44 may ascertain the respective impedances between the electrode and multiple external electrodes 52 on the body surface of subject 24 at various different locations, and then compute the ratios between these impedances in order to find the electrode location. As yet another alternative, the controller 44 may use both electromagnetic tracking and impedance-based tracking, as described, for example, in U.S. Pat. No. 8,456,182, whose disclosure is incorporated herein by reference.

In some embodiments, controller 44 ascertains which of ablation electrodes 30 are in contact with the subject's tissue, and applies ablation signals 40 through those electrodes, but not the other electrodes. In other words, the controller 44 selects a subset of channels leading to those electrodes that are in contact with the tissue, and then directs signals 40 to be passed over the selected subset of channels, but not over the other channels.

In some embodiments, controller 44 displays, on display 48, a relevant image 54 of the subject's anatomy, annotated, for example, to show the current position and orientation of distal portion 28. Alternatively or additionally, based on signals received from relevant sensors disposed on distal portion 28, controller 44 may track the temperature and/or impedance of tissue 36, and control signal generator 38 responsively thereto. Alternatively or additionally, controller 44 may perform any other relevant function for controlling, or otherwise facilitating the performance of, the procedure.

Controller 44 and signal generator 38 typically reside within a console 56, and both the controller and the signal generator may each comprise one or several units. Catheter 26 is connected to console 56 via an electrical interface 58, such as a port or socket. Signals 40 are thus carried to distal portion 28 via interface 58. Similarly, signals for tracking the position of distal portion 28 and/or signals for tracking the temperature and/or impedance of the tissue may be received by controller 44 via interface 58. Magnetic-field generators 50 and external electrodes are connected to console 56 via cables 60 and 62, respectively.

Controller 44 typically comprises both analog and digital elements. Thus, controller 44 may comprise multiple analog-to-digital converters (ADCs) for receiving analog signals from catheter 26 and from signal generator 38. Controller 44 may further comprise multiple digital-to-analog converters (DACs) for transmitting analog control signals to signal generator 38 and other system components. Alternatively, these control signals may be transmitted in digital form, provided that signal generator 38 is configured to receive digital control signals. Controller 44 typically comprises digital filters for extracting signals at given frequencies from the received signals.

Typically, the functionality of controller 44, as described herein, is implemented at least partly in software. For example, controller 44 may comprise a programmed digital computing device comprising at least a central processing unit (CPU) and random access memory (RAM). Program code, including software programs and/or data are loaded into the RAM for execution and processing by the CPU. The program code and/or data may be downloaded to the controller in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Notwithstanding the particular type of cardiac ablation procedure illustrated in FIG. 1, the principles of the embodiments described herein may be applied to any suitable type of ablation procedure.

Figure 2A:
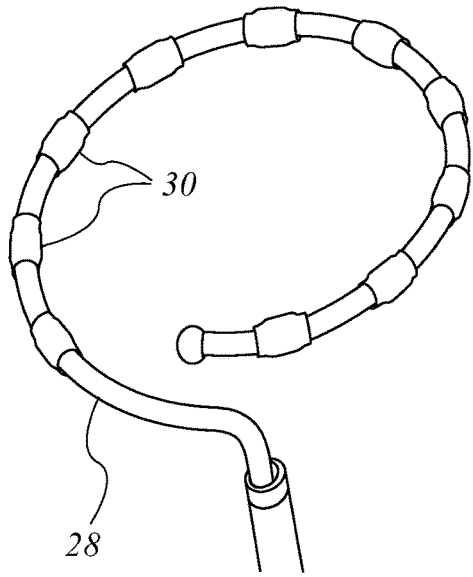
FIGS. 2A and 2B are schematic pictorial illustrations of a distal portion of a catheter, in accordance with an exemplary embodiment of the invention.
Figure 2B:
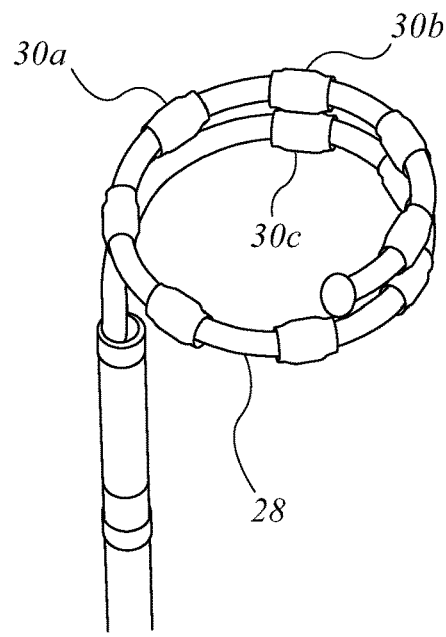

FIGS. 2A and 2B illustrate two shapes of distal portion 28 of catheter 26, in accordance with an embodiment of the invention. Items similar to those in FIG. 1 are marked with the same labels. Catheter 26 is of the "Lasso" type, with multiple electrodes 30 mounted on distal portion 28.

In FIG. 2A, distal portion 28 forms a loop, but without any of electrodes 30 coming into contact with or proximity to any of the other electrodes. In FIG. 2B, distal portion 28 forms a tighter loop than in FIG. 2A, with an electrode 30c coming into contact with or close proximity to an electrode 30b. Utilizing the pair of electrodes 30a and 30b for ablation will cause at least some of the current flowing through electrode 30b to leak parasitically through electrode 30c. As a result of the reduction in power that is actually applied to the tissue, the ablation between electrodes 30a and 30b is likely to be inadequate.

Figure 3:
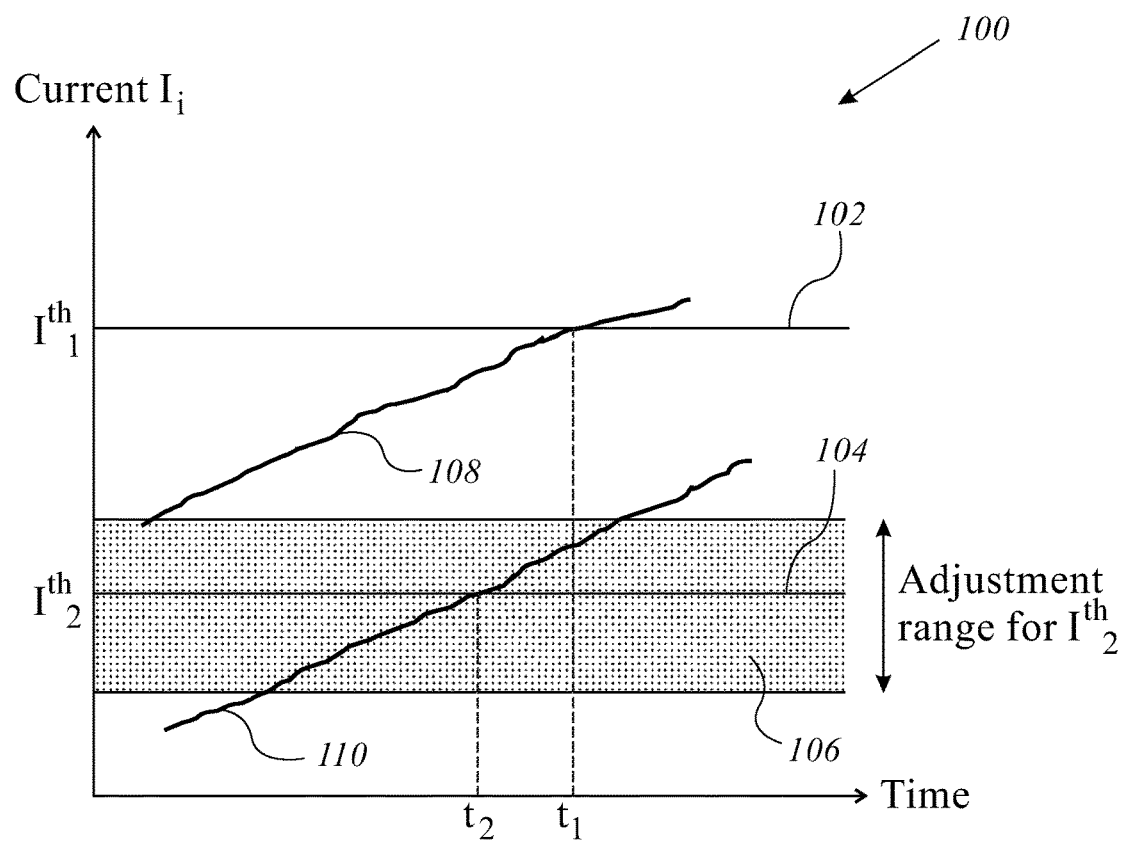
FIG. 3 is a plot of parasitic current flow through an electrode over time during an ablation procedure, illustrating schematically thresholds for leaked current, in accordance with an exemplary embodiment of the invention.

FIG. 3 is a plot 100 of parasitic current flow through an electrode over time during an ablation procedure, illustrating schematically thresholds for leaked current, in accordance with an embodiment of the invention. The electrode in question is assumed to be one of electrodes 30 on catheter 26, such as electrode 30c in the preceding figure, that is not a part of the electrode pair through which the ablation current is intended to flow.

Plot 100 shows a first threshold $I^{th}_1$ marked by a line 102, and a second threshold $I^{th}_2$, marked by a line 104. In addition, plot 100 shows an adjustment range 106 for second threshold $I^{th}_2$, within which physician 22 may set the second threshold. The vertical axis of plot 100 indicates current $I_i$, wherein the subscript i refers to any electrode 30 that is not one of the two electrodes selected for ablation (such as 30a and 30b in FIGS. 1 and 2B). For brevity, only one plot is shown, whereas, for example for catheter 26 with ten electrodes 30, there will be eight electrodes not participating in the ablation.

For illustration, two example currents $I_i$, current 108 and current 110 are shown. In the first example, current 108 exceeds first threshold $I^{th}_1$ at a time $t_1$. At this time, controller 44 issues a notification indicative of a possible short-circuit between electrode i and one of the ablation electrodes. Physician 22 may assume that the ablation has been inadequate, and he/she may take an action such as adjusting catheter 26, and repeating the ablation.

In the second example, current 110 exceeds second threshold $I^{th}_2$ at a time $t_2$. At this time, controller 44 issues a notification indicating that a parasitic current flow has been detected, leading to the possibility that the tissue was inadequately ablated. The notification enables physician 22 to accept or reject the ablation, for example by testing whether a current block has been established in the tissue at the location of the ablation. If physician determines that ablation was inadequate, he/she can repeat the ablation as necessary. Physician 22 may also adjust second threshold $I^{th}_2$ within range 106 or leave it at its current value. For example, if the ablation was found to be adequate notwithstanding the notification, physician 22 may choose to reduce $I^{th}_2$ in order to avoid further false alarms.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical apparatus for performing ablation, comprising:
   a probe configured for insertion into a body of a patient and comprising three or more electrodes arrayed along a distal portion of the probe and configured to contact tissue within the body, wherein the distal portion is configured to be flexible;
   an electrical signal generator configured to apply, between a selected pair of the electrodes, signals having an amplitude sufficient to ablate the tissue contacted by the pair of the electrodes; and
   a controller, which is configured to identify physical contact or physical proximity between one electrode of the selected pair and a third electrode not included in the selected pair due to bending of the distal portion, wherein identifying the physical contact or physical proximity is based on measuring an electrical current flowing through the third electrode while applying the signals to the selected pair, and to issue a notification indicating that the tissue was inadequately ablated due to the physical contact or physical proximity if the measured electrical current on the third electrode exceeds a preset threshold.

2. The apparatus according to claim 1, wherein the controller is configured to issue a first notification indicating that the tissue was inadequately ablated if the measured electrical current exceeds a first threshold, and to issue a second notification indicative of a parasitic current flow between the third electrode and one of the selected pair of the electrodes when the measured electrical current does not exceed the first threshold but does exceed a second threshold, which is lower than the first threshold.

3. The apparatus according to claim 2, wherein the second threshold is less than half the first threshold.

4. The apparatus according to claim 2, wherein the second threshold is adjustable by a user.

5. The apparatus according to claim 1, wherein the controller is configured to measure and monitor respective currents flowing through multiple electrodes that are not in the selected pair.

6. The apparatus according to claim 1, wherein the amplitude of the signals is sufficient to cause irreversible electroporation (IRE) of the tissue contacted by the selected pair of the electrodes.

7. The apparatus according to claim 1, wherein the distal portion is configured for insertion into a heart of the patient.

8. The apparatus according to claim 7, wherein the distal portion is configured to form a loop within the heart.

9. A method for medical treatment, comprising:
   inserting a probe into a body of a patient, wherein the probe comprises three or more electrodes arrayed along a distal portion of the probe, wherein the distal portion is configured to be flexible;
   bringing a selected pair of the electrodes of the probe into contact with tissue within the body;
   applying between the selected pair of the electrodes signals having an amplitude sufficient to ablate the tissue contacted by the selected pair;
   identify physical contact or physical proximity between one electrode of the selected pair and a third electrode not included in the selected pair due to bending of the distal portion, wherein identifying the physical contact or physical proximity is based on measuring an electrical current flowing through the third electrode while applying the signals to the selected pair; and
   issuing a notification indicating that the tissue was inadequately ablated due to the physical contact or physical proximity if the measured electrical current on the third electrode exceeds a preset threshold.

10. The method according to claim 9, wherein issuing the notification comprises issuing a first notification indicating that the tissue was inadequately ablated if the measured electrical current exceeds a first threshold, and the method comprises issuing a second notification indicative of a parasitic current flow between the third electrode and one of the selected pair of the electrodes when the measured electrical current does not exceed the first threshold but does exceed a second threshold, which is lower than the first threshold.

11. The method according to claim 10, wherein the second threshold is less than half the first threshold.

12. The method according to claim 10, and comprising adjusting the second threshold in response to an input by a user.

13. The method according to claim 9, wherein measuring the electrical current comprises measuring and monitoring respective currents flowing through multiple electrodes that are not in the selected pair.

14. The method according to claim 9, wherein the amplitude of the signals is sufficient to cause irreversible electroporation (IRE) of the tissue contacted by the selected pair of the electrodes.

15. The method according to claim 9, wherein the distal portion is configured to be inserted into a heart of the patient.

16. The method according to claim 15, and wherein the distal portion is configured to form a loop within the heart.

* * * * *